United States Patent
Greenway et al.

(12)

(10) Patent No.: US 6,765,007 B1
(45) Date of Patent: Jul. 20, 2004

(54) HIGH-CONTENT FAMCICLOVIR TABLETS

(75) Inventors: Michael John Greenway, Worthing (GB); Jennifer Mary Slater, Brighton (GB)

(73) Assignee: Novartis International Pharmaceutical Ltd., Hamilton (BM)

( * ) Notice: Subject to any disclaimer, the term of this patent is extended or adjusted under 35 U.S.C. 154(b) by 350 days.

(21) Appl. No.: 09/101,926

(22) PCT Filed: Jan. 13, 1997

(86) PCT No.: PCT/EP97/00195

§ 371 (c)(1),
(2), (4) Date: Sep. 24, 1998

(87) PCT Pub. No.: WO97/25990

PCT Pub. Date: Jul. 24, 1997

(30) Foreign Application Priority Data

Jan. 16, 1998 (GB) .............................. 9600847

(51) Int. Cl.⁷ .............................. A61K 31/52

(52) U.S. Cl. ....................................... 514/261
(58) Field of Search ........................ 514/261

(56) References Cited

U.S. PATENT DOCUMENTS 5,556,639 A * 9/1996 Fielden ....................... 424/480

FOREIGN PATENT DOCUMENTS

| EP | 0 182 024 A2 | 5/1986 | ......... C07D/473/32 |
| EP | 0 615 750 A2 | 9/1994 | ......... A61K/31/00 |
| FR | 2 671 970 A | 7/1992 | ............ A61K/9/20 |
| WO | WO 92/20816 | 11/1992 | |
| WO | WO 95/09632 | 4/1995 | |

* cited by examiner

Primary Examiner—Russell Travers
(74) Attorney, Agent, or Firm—Thomas R. Savitsky

(57) ABSTRACT

A pharmaceutical tablet wherein famciclovir is the active ingredient and wherein the percentage of famciclovir by weight in the tablet is 85% or greater.

9 Claims, No Drawings

HIGH-CONTENT FAMCICLOVIR TABLETS

This is a §371 national stage entry of International Application PCT/EP97/00195, Jan. 13, 1997.

This invention relates to a novel formulation of a pharmaceutical product.

EP-A-182024 (Beecham Group p.l.c.), Example 2 describes a method of the preparation of famciclovir, a compound which is useful as the oral form of the compound, penciclovir which has antiviral activity against infections caused by herpesviruses, such as herpes simplex type 1, herpes simplex type 2 and varicella zoster virus, and also against Hepatitis B virus. Penciclovir and its antiviral activity is disclosed in Abstract P.V11-5 p.193 of 'Abstracts of 14th Int. Congress of Microbiology', Manchester, England Sep. 7–13, 1986 (Boyd et. al.).

Famciclovir is preferably administered in the form of tablets containing 125 mg, 250 mg, 500 mg or 750 mg of active ingredient. As is conventional in tablet compositions, the tablets contain excipients such as lactose, sodium starch glycollate and magnesium stearate such that the total excipient content is at least 15%. Anhydrous lactose is conventionally included as a major excipient to compensate for any potential inconsistencies in the compression properties of the active ingredient.

The higher the percentage excipient content, the greater the tablet size for a tablet of any given dosage. Particularly in the case of tablets containing 500 mg and 750 mg of active ingredient, the large tablet size can affect patient compliance as the oval face of the tablet would measure 18 mm×8.5 mm and 21 mm×10 mm respectively when the tablet contains about 76% famciclovir.

It has been discovered that it is possible to formulate famciclovir into a tablet containing less than 15% excipients as the compression properties of famciclovir have proved to be sufficiently consistent to permit this.

Accordingly, the present invention provides a pharmaceutical tablet wherein famciclovir is the active ingredient and wherein the percentage of famciclovir by weight in the tablet is 85% or greater.

All values for percentage weight given herein unless otherwise stated are defined in terms of the core of any tablet which may be coated, for example, film coated.

A suitable tablet contains less than 15%, less than 10%, less than 5% and preferably 0% of anhydrous lactose or other similar excipient such as microcrystalline cellulose.

A suitable tablet contains famciclovir at a percentage weight of greater than 85%, 86%, 87%, 88%, 89%, 90% or 91%. The highest possible percentage of famciclovir is preferred. Famciclovir may be in any suitable pharmaceutically acceptable form, such as in the form of a salt, solvate or polymorph. Famciclovir is preferably in an anhydrous, free base form.

Conventional excipients included in the composition of the tablet include hydroxypropyl cellulose, for example up to 5% or up to 3%, sodium starch glycollate, for example up to 15%, 10%, 7% or 5% and magnesium stearate, for example up to 2% or 1%.

The tablets may be coated with any suitable coating used for pharmaceutical tablets.

The tablets may be prepared by conventional compression methods known in the art. In a preferred method, famciclovir is granulated with an excipient such as hydroxypropyl cellulose, in order to minimise the effect of any variations in physical form of the active ingredient. The granules are screened and dried and then blended with any further excipients to form a compression mix. Tablets are compressed to the size and weight appropriate to the required dosage and then optionally coated as desired.

The following Example illustrates the invention.

EXAMPLE

The percentage values in brackets indicate the percentage values in the famciclovir tablets currently registered by the regulatory authorities for pharmaceuticals, in the United Kingdom of Great Britain and Northern Ireland, the U.S.A and other countries of the world.

| Constituent | % w/w | % w/w |
|---|---|---|
| Famciclovir | 91.42 | (75.66) |
| Hydroxypropyl cellulose | 2.83 | (2.34) |
| sodium starch glycolate | 5.00 | (5.00) |
| magnesium stearate | 0.75 | (0.75) |
| anhydrous lactose | 0 | (16.25) |

Approximate Core Weight is 547 mg for 500 mg dosage and 820 mg for 750 mg dosage.

For coated tablets, 2.5% of core weight is added by the coating and the coated tablet weighs 560 mg for the 500 mg dosage and 840 mg for the 750 mg dosage.

The tablets are prepared by dry mixing famciclovir with hydroxypropyl cellulose and then granulating the mixture with water in a high shear granulator. The wet mass is screened, dried and milled. The milled granules are blended with sodium starch glycollate and magnesium stearate to produce the compression mix. Tablets are compressed at the size and weight appropriate to the required strength of tablet and then aqueous film coated.

The resulting size of an oval face of a 750 mg tablet is 19 mm×9 mm and of a 500 mg tablet is 17 mm×8 mm.

What is claimed is:

1. A pharmaceutical tablet, for oral administration directly, wherein the tablet contains as an active ingredient, famciclovir, and wherein the percentage of famciclovir by weight in the tablet is 85% or greater.

2. A pharmaceutical tablet according to claim 1, containing less than 15% lactose.

3. A pharmaceutical tablet according to claim 2, containing less that 5% lactose.

4. A pharmaceutical tablet according to claim 3, containing 0% lactose.

5. A pharmaceutical tablet according to claim 1 where in the percentage of famciclovir by weight in the tablet is 90% or greater.

6. A pharmaceutical tablet according to claim 1 having the following composition:

| Constituent | % w/w |
|---|---|
| Famciclovir | 91.42 |
| Hydroxypropyl cellulose | 2.83 |
| sodium starch glycolate | 5.00 |
| magnesium stearate | 0.75 |
| anhydrous lactose | 0. |

7. A process for the preparation of a tablet according to claim 1, wherein the famciclovir and excipients are granulated and then compressed to form a tablet.

8. A process according to claim 7, wherein the famciclovir is granulated with hydroxypropyl cellulose, blended with any further excipients and then compressed to form a tablet.

9. A pharmaceutical tablet according to claim 1, containing 500 mg or 750 mg of famciclovir.

* * * * *

UNITED STATES PATENT AND TRADEMARK OFFICE
CERTIFICATE OF CORRECTION

PATENT NO. : 6,765,007 B1
DATED : July 20, 2004
INVENTOR(S) : Greenway et al.

It is certified that error appears in the above-identified patent and that said Letters Patent is hereby corrected as shown below:

<u>Title page,</u>
Item [30], Foreign Application Priority Data, should read:
-- Jan. 16, 1996      (GB) ……………...9600847 --.

Signed and Sealed this

Thirtieth Day of November, 2004

JON W. DUDAS
*Director of the United States Patent and Trademark Office*